(12) United States Patent
Kirsch et al.

(10) Patent No.: US 6,787,062 B2
(45) Date of Patent: Sep. 7, 2004

(54) PRODUCING LIQUID CRYSTALS WITH CF$_2$O BOND

(75) Inventors: Peer Kirsch, Darmstadt (DE); Andreas Taugerbeck, Darmstadt (DE); Detlef Pauluth, Ober-Ramstadt (DE); Matthias Bremer, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/220,428

(22) PCT Filed: Mar. 2, 2001

(86) PCT No.: PCT/EP01/02402

§ 371 (c)(1),
(2), (4) Date: Sep. 3, 2002

(87) PCT Pub. No.: WO01/64667

PCT Pub. Date: Sep. 7, 2001

(65) Prior Publication Data

US 2003/0069433 A1 Apr. 10, 2003

(30) Foreign Application Priority Data

Mar. 3, 2000 (DE) .......................................... 100 10 537
May 31, 2000 (DE) .......................................... 100 27 102

(51) Int. Cl.[7] .................... C09K 19/30; C07D 339/00; C07D 341/00; C07C 17/02

(52) U.S. Cl. .................... 252/299.63; 428/1.1; 549/21; 549/22; 549/20; 549/35; 549/36; 549/39; 570/126

(58) Field of Search ..................... 252/299.63; 428/1.1; 549/21, 22, 20, 35, 36, 39; 570/126

(56) References Cited

U.S. PATENT DOCUMENTS 4,726,911 A * 2/1988 Krause et al. ......... 252/299.61
6,187,223 B1 * 2/2001 Andou et al. ......... 252/299.63

FOREIGN PATENT DOCUMENTS

EP    0 844 229 A1    5/1998

OTHER PUBLICATIONS

Okuyama et al., "Mechanism of Hydrolysis of 1,3–Dithiane Derivatives. Breakdown of the Tetrahedral Intermediates," *J. Org. Chem.,* 1986, vol. 51, pp. 4988–4990.

Okuyama et al., "Mechanism of Hydrolysis of 2–tert–Butyl–2–methoxy–1,3dithiolane. Rate–Determining Deprotonation in the Breakdown of Tetrahedral Intermediate," *J. Am. Chem. Soc.,* vol. 107, No. 14, 1985, pp. 4224–4229.

Bellsia et al., "γ–Alkylketene Dithloacetals From 2,3–Dichloroaldehyde Dithloacetals," *Gazzetta Chimica Italiana,* vol. 125, No. 10, 1995, pp. 501–504.

Sondej et al., "gem–Difluoro Compounds: A Comvenient Preparation from Ketones and Aldehydes by Halogen Fluoride Treatment of 1,3–Dithlolanes," *J. org. Chem.,* vol. 51, No. 18, 1986, pp. 3508–3513.

* cited by examiner

Primary Examiner—Deborah C. Lambkin
(74) Attorney, Agent, or Firm—Millen, White, Zelano & Branigan, P.C.

(57) ABSTRACT

The invention relates to a process for the preparation of compounds having at least one —CF$_2$O— bridge in the molecule, which comprises initially reacting a bis(alkylthio) carbenium salt with a compound containing at least one hydroxyl group in the presence of a base followed by oxidative fluorination, preferably in situ, with a fluorinating agent and an oxidizing agent to form the compound having at least one —CF$_2$O— bridge in the molecule.

9 Claims, No Drawings

PRODUCING LIQUID CRYSTALS WITH CF₂O BOND

The invention relates to a process for the preparation of compounds having at least one —CF$_2$O— bridge in the molecule.

Liquid crystals have been widely used ever since the first commercially useful liquid-crystalline compounds were discovered about 30 years ago. Typical application areas are in particular displays for watches and clocks or pocket calculators, or large display panels as used in railway stations, airports or sports arenas. Other application areas are displays of portable computers or navigation systems, and video applications. The latter applications in particular have to meet high requirements on switching times and image contrast.

The liquid-crystalline molecules must have certain properties to be useful for commercial applications. To be able to use devices having a liquid-crystal display under various climatic conditions, the molecules must form a stable nematic phase over a very wide temperature range including the room temperature range. The compounds must therefore have a low melting point and a high clearing point.

To be able to realize low switching times, the molecules must have a low rotational viscosity. For example, switching times of less than 16.7 ms are required for video applications. The liquid-crystalline molecules should furthermore have a high dielectric anisotropy so that only low threshold voltages are required. This means that little energy is required so that it is possible to use smaller and lighter accumulators, for example in laptops. Another important factor for the design of the display are the birefringence properties of the molecules which have an effect on contrast and available viewing angle.

To be able to satisfy all these requirements simultaneously, mixtures which often comprise 5 to 15 different components are employed rather than pure substances. This means that the individual components have to be compatible with one another, i.e. are sufficiently soluble in one another, for example.

High image contrast is desired for modern active-matrix displays. The liquid-crystalline compounds must therefore have a high resistivity and a high voltage holding ratio.

Liquid-crystalline compounds which have been found to have a particularly high resistivity are those which contain fluorine-containing groups in their molecular framework. For example, EP 0 844 229 A1 describes liquid-crystalline compounds which contain an —O—CF$_2$— bridge. Various methods for obtaining this —O—CF$_2$— bridge are suggested. One of the methods described involves initially converting an aromatic halide into a Grignard compound or a lithiated compound followed by conversion into the the dithiocarboxylic acid by means of carbon disulfide. The dithiocarboxylic acid is then converted into a thioester using a phenol in the presence of an alkali metal hydride and iodine. The desired —O—CF$_2$— bridge is then formed from the thioester using a fluorinating agent.

Another method which is suggested involves initially reacting a cyclohexanone with tris(dimethylamino) phosphine and dibromodifluoromethane to obtain a difluoromethylenehexylidene. A —CF$_2$—O— bridge is then formed by addition of bromine to this derivative followed by etherification by reacting with a phenolate with simultaneous elimination of hydrogen bromide.

Disadvantages of these processes are low reaction rates, unsatisfactory yields and complicated work-up and purification.

It is therefore an object of the invention to provide a process for the preparation of compounds having at least one —CF$_2$O— bridge in the molecule which produces good yields at a satisfactory reaction rate. Intermediates and final products should be easy to purify.

This object is achieved by the process according to the invention, which comprises initially reacting a bis(alkylthio) carbenium salt with a compound containing at least one hydroxyl group in the presence of a base followed by oxidative fluorination, preferably in situ, with a fluorinating agent and an oxidizing agent to form the compound having at least one —CF$_2$O— bridge in the molecule.

The bis(alkylthio)carbenium salts can be prepared very easily from the corresponding carboxylic acids or activated carboxylic acid derivatives. Examples of suitable carboxylic acid derivatives include carbonyl halides, carbonyl pseudohalides, suitably substituted carbonyl sulfonylates, such as a trifluoromethylsulfonylate. Furthermore, carboxylic anhydrides and alkyl- or phenylcarboxylic esters can be used. The salts precipitate in clean form from the reaction solution and can be employed in the next stage without further purification.

The bis(alkylthio)carbenium salt is initially reacted with the compound containing at least one hydroxyl group to produce a dithioorthoester. This dithioorthoester is generally not isolated, but immediately reacted further. The oxidative fluorination to form the compound having a —CF$_2$O— group is conducted under very mild, slightly basic conditions and is therefore compatible with numerous unprotected functional groups, for example a nitrile group, in contrast to the conventional methods. Another advantage is that the stereochemistry of the radicals, for example a cis-oder trans-cyclohexylene radical, is retained in the reaction. The principal steps are summarized in FIG. 1 below.

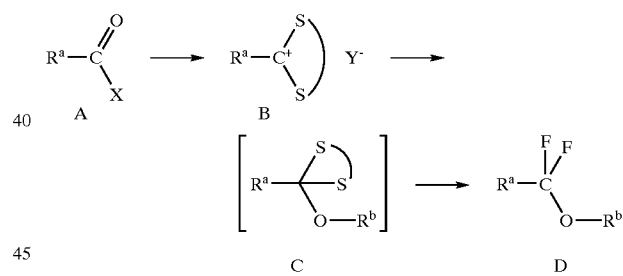

FIG. 1 Reaction scheme for the preparation of compounds having a CF$_2$O bridge.

The carboxylic acid derivative A, in which X is, for example, —OH, halogen, pseudohalogen, substituted sulfonate, an anhydride, alkoxy or phenoxy, is then reacted with an alkylthiol to give the bis(alkylthio)carbenium salt B. Preference is given to using dithiols which lead to the formation of a cyclic cation. Particularly suitable thiols are therefore ethanedithiol, propanedithiol or 1,2-benzenedithiol which lead to the formation of dithianylium and dithiolanylium salts, respectively. This salt B is then reacted with a hydroxyl compound R$^b$—OH to give an orthoester C. The orthoester C is generally not isolated, but directly oxidized to give compound D. The process is universally applicable so that R$^a$ and R$^b$ are not subject to any restrictions per se. For example, R$^a$ and R$^b$, independently of one another, can be an alkyl, aryl, cycloalkyl or alkenyl radical, where these radicals in turn may be substituted as desired, for example by halogen, pseudohalogen, hydroxyl or carbonyl groups.

For the preparation of liquid crystals it is preferred that the bis(alkylthio)-carbenium salt has a structure of the formula I.

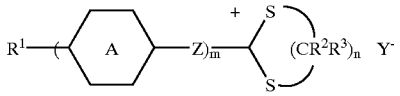

in which:

in each case independently of one another, is cis- or trans-1,4-cyclohexylene, 1,4-phenylene or 1,4-cyclohex-3-enylene, where these groups may also be monosubstituted or disubstituted by halogen, in particular fluorine, pseudohalogen, —OCF$_3$ or —OCHF$_2$, $R^1$ is a linear or branched alkyl or alkoxy radical having 1 to 12 carbon atoms which is unsubstituted, monosubstituted by —CN or —CF$_3$ or at least monosubstituted by halogen, a linear or branched oxyalkyl, alkenyl or alkenyloxy radical having 2 to 12 carbon atoms or a linear or branched oxalkenyl radical having 3 to 12 carbon atoms, where, in addition, one or more CH$_2$ groups in these radicals may, in each case independently of one another, be replaced by —O—, —S—, —CO—, —CO—O—, —O—CO— or —O—CO—O— in such a way that heteroatoms are not linked directly to one another, or halogen, preferably F or Cl, Z is, in each case independently of one another, a single bond, a —CH$_2$—CH$_2$—, —CF$_2$—CF$_2$—, —CF$_2$—CH$_2$—, —CH$_2$—CF$_2$—, —O—CO—, —CF=CF—, —CH=CH—, —C≡C—, —CO—O—, —O—CO—, —CF$_2$—O— or —O—CF$_2$— group, —S—(CR$^2$R$^3$)$_n$—S— is a bridge consisting of two sulfur atoms which are linked by a carbon chain having two or three carbon atoms, where the hydrocarbon bridge may also carry one or more substituents R$^2$ and R$^3$, in particular alkyl or alkylene groups, where, in addition, the radicals R$^2$ and R$^3$ may together form a cycloalkyl group or aryl group,

| | |
|---|---|
| m | is an integer from 0 to 6, |
| n | is 2 or 3, and |
| Y$^-$ | is any desired anion. |

The process according to the invention is generally suitable for the preparation of compounds having a —CF$_2$—O— bridge, such as liquid crystals, intermediates for polymers, pharmaceuticals and crop protection agents, for example. However, it is particularly suitable for the preparation of liquid-crystalline compounds. As a fragment which is adjacent to the —CF$_2$—O— bridge on one side is introduced into the molecule by means of the bis(alkylthio) carbenium salt B, the radicals R$^1$ are preferably structural elements customary in liquid-crystalline compounds. Some fragments of this type are listed by way of example in FIG. 2, this list not being exhaustive. R is as defined for R$^1$ above.

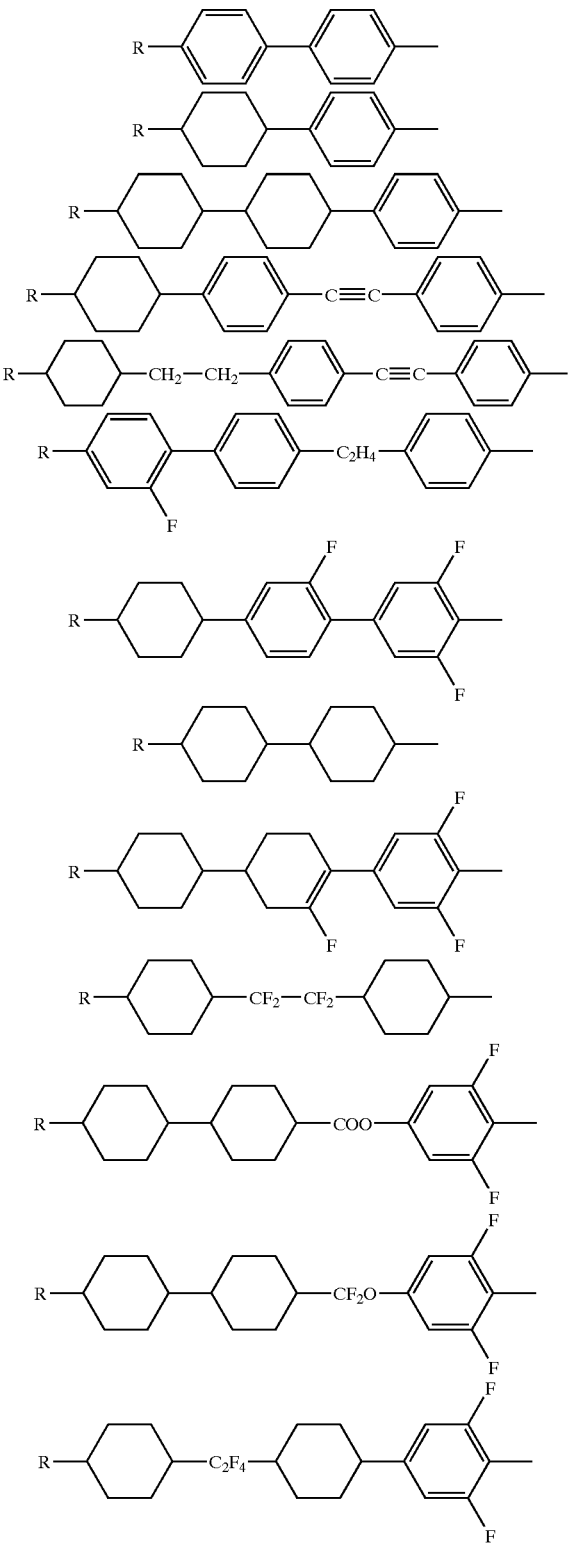

FIG. 2 Examples of building blocks customary in liquid-crystalline compounds.

The compound containing at least one hydroxyl group is preferably a phenol which may optionally be substituted, and in particular carries a polar group, preferably —F, —Cl, —CN, —NCS, —OCF$_3$ or —OCH$_2$F, or an alkyl, cycloalkyl or phenyl radical in 4-position, which radicals in turn may be substituted by alkyl, cycloalkyl or phenyl radicals, where, in addition, hydrogen atoms may also be substituted by fluorine or chlorine atoms and in each case a —CH$_2$—CH$_2$—, —CF$_2$—CF$_2$—, —CF$_2$—CH$_2$—, —CH$_2$—CF$_2$—, —CF=CF—, —CH=CH—, —C≡C—, —COO—, —O—CO—, —O—CF$_2$— or —CF$_2$—O— group may be present between these groups.

The structure of the compound containing at least one hydroxyl group is not subject to any particular restrictions per se. However, as the process according to the invention is particularly suitable for the preparation of liquid crystals, the radical present in the compound containing at least one hydroxyl group preferably contains structural elements customary in liquid crystals. Examples of structural elements which may be mentioned are again the building blocks depicted in FIG. 2.

The bis(alkylthio)carbenium salt preferably contains a noncoordinating or weakly coordinating anion, in particular selected from the group consisting of tetrafluoroborate, hexafluorophosphate, perchlorate and perfluoroalkylsulfonate, in particular trifluoromethanesulfonate. Owing to their very low hygroscopicity, these salts are easy to process.

The oxidizing agent used can be any customary oxidizing agent. The oxidizing agent used is preferably a compound which releases halonium equivalents. Examples of oxidizing agents are N-bromosuccinimide, N-iodosuccinimide, 1,3-dibromo-5,5-dimethylhydanthoin and bromine. Particular preference is given to bromine, since the resulting bromides are easy to remove. Other examples of suitable oxidizing agents are SO$_2$Cl$_2$, SO$_2$ClF, nitrosonium and nitronium salts and Chloramin T.

The fluorinating agent used can be any customary fluorinating agent. The fluorinating agent is particular preferably selected from the group consisting of aliphatic and aromatic amine/hydrogen fluoride complexes, for example pyridine/hydrogen fluoride complexes, NEt$_3$·3HF, 50% HF in pyridine, melamine-HF and polyvinylpyridine-HF.

As already mentioned above, the process according to the invention is particularly suitable for the preparation of liquid crystals. The process according to the invention utilizes bis(alkylthio)carbenium salts as starting materials. The invention therefore also relates to bis(alkylthio)carbenium salts of the formula I.

in which R$^1$,

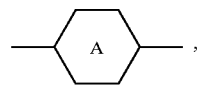

Z, —S—(CR$^2$R$^3$)$_n$—S—, m, n and Y$^-$ are as defined above.

The invention furthermore relates to dithioorthoesters of the formula II

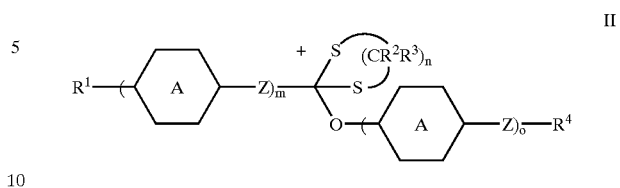

in which R$^1$, R$^2$, R$^3$, Z,

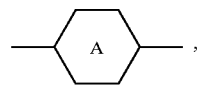

m and n are as defined in claim 2, and R$^4$ is as defined for R$^1$ in claim 2, and, in addition, may be —H, —F, —Cl, —CN, —SCN, —OCF$_3$ or —OCHF$_2$, and o is an integer between 0 and 6.

The invention is illustrated below by means of examples.

EXAMPLE 1

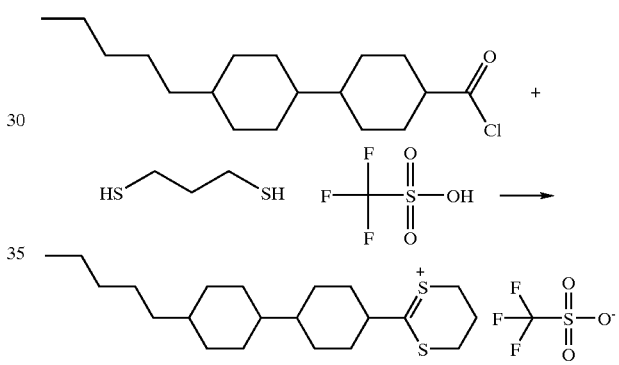

2 ml of 1,3-propanedithiol were added to 5.9 g of, 4-(4'-pentylcyclohexyl)cyclohexanecarbonyl chloride with ice cooling. 2.6 ml of trifluoromethanesulfonic acid were then added, the mixture was heated to 110° C. and stirred for 15 minutes. The reaction mixture was removed from the heating bath and slightly cooled. The reaction mixture was then dissolved in 10 ml of acetonitrile and poured onto 200 ml of ether. The colourless crystals which had precipitated were filtered off with suction under nitrogen and dried in vacuo.

Yield: 3.0 g. After storage of the mother liquor at 0° C., another 3.1 g of product were isolated.

$^{13}$C NMR (CDCl$_3$, 303 K): δ$_{carbenium}$=203.5 ppm.

EXAMPLE 2

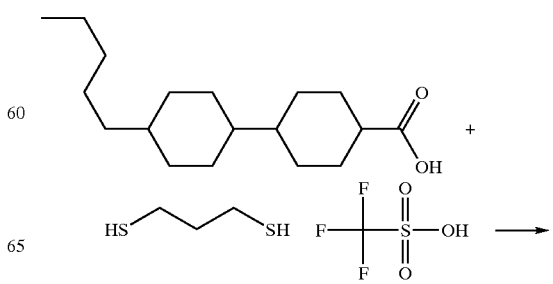

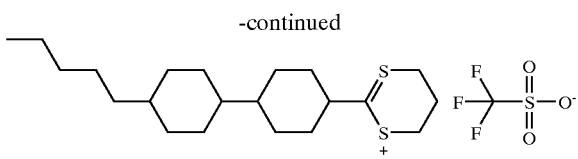

10 g of 4-(4'-pentylcyclohexyl)cyclohexanecarboxylic acid were admixed with 3.6 ml of 1,3-propanedithiol and cooled in an ice bath. 7.9 ml of trifluoromethanesulfonic acid were added. After addition was complete, the mixture was heated to 120° C. and stirred for 30 minutes. The reaction mixture was removed from the heating bath and dissolved in 10 ml of acetonitrile. The solution was poured onto 50 ml of ice-cold ether, and colourless platelets precipitated. The mixture was cooled to −20° C. for another 2 hours and then filtered with suction under nitrogen. Drying in vacuo yielded colourless platelets.

Yield: 10.9 g (60.2% of theory)
$^{13}$C NMR (CDCl$_3$, 303 K): $\delta_{carbenium}$=203.5 ppm.

EXAMPLE 3

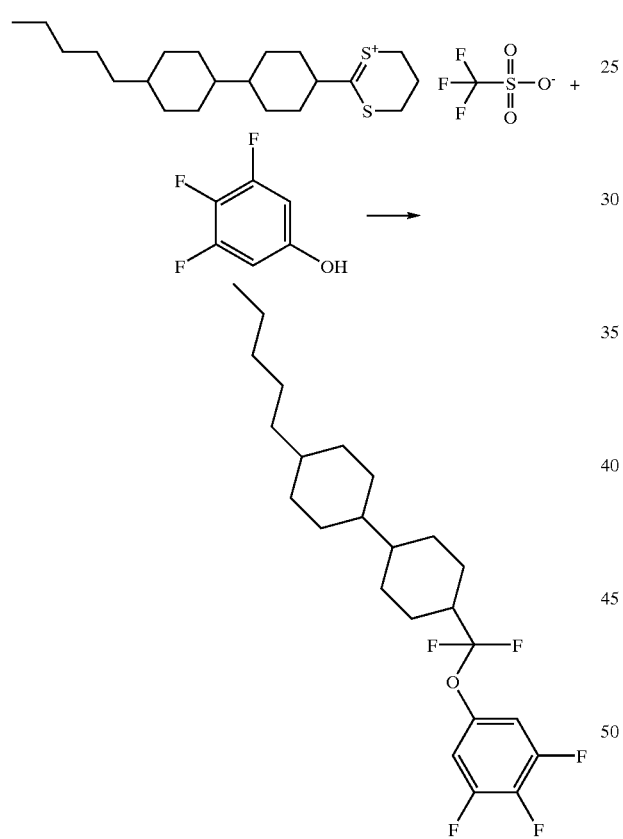

1.06 g of the dithianylium trifluoromethanesulfonate obtained in Example 2 were initially charged in 20 ml of dichloromethane at −70° C. and admixed with a mixture of 0.6 ml of triethylamine and 0.7 g of trifluorophenol (90% in toluene) in 2 ml of dichloromethane, which resulted in immediate precipitation of a colourless solid. The reaction mixture was stirred for 2 hours at −70° C. Subsequently 3 g of 1,3-dibromo-5,5-dimethylhydanthoin, suspended in 15 ml of dichloromethane, were added in portions over the course of 20 minutes. The reaction mixture was stirred at −70° C. for another 90 minutes and then warmed to room temperature. The solution was poured onto saturated sodium hydrogencarbonate solution with stirring, the organic phase was separated and the aqueous phase was extracted twice with dichloromethane. The combined organic phases were dried and the solvent was removed in vacuo. Filtration through silica gel yielded a colourless oil which slowly crystallized.

Yield: 415 mg (45.5% of theory)
Melting point: 59° C.
Clearing point: 112° C.

EXAMPLE 4

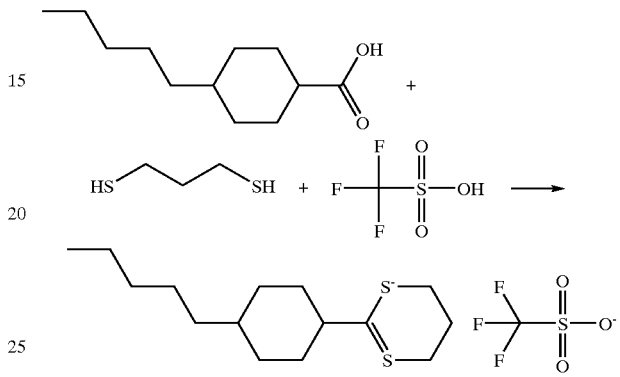

199 g of 4-pentylcyclohexanecarboxylic acid were admixed with 100 ml of 1,3-propanedithiol and cooled in an ice bath. 263 mg of trifluoromethanesulfonic acid were added dropwise. After addition was complete, the reaction mixture was heated to 120° C. for 1 hour. The reaction mixture was cooled to about 70° C. and then poured onto 500 ml of ice-cold dibutyl ether, and the solution was cooled to −20° C. overnight. The crystals which had precipitated were filtered off with suction, washed with ether and dried in vacuo.

Yield: 92 g (21.9% of theory).

EXAMPLE 5

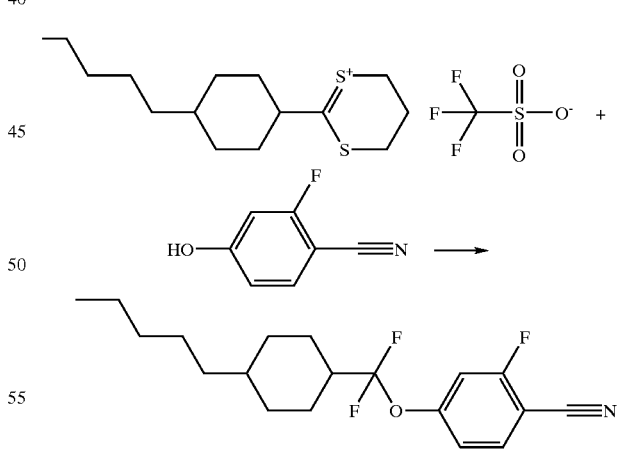

30 g of the dithianylium trifluoromethanesulfonate obtained in Example 4 were intially charged in 250 ml of dichloromethane at −70° C. A solution of 14.8 ml of triethylamine and 12.2 g of 3-fluoro-4-cyanophenol in 50 ml of dichloromethane was added dropwise at −70° C., which resulted in immediate precipitation of a colourless solid. The reaction mixture was stirred for another hour at −70° C. 57.2 ml of triethylamine tris-hydrofluoride were added dropwise and the mixture was stirred for another 5 minutes. 18.2 ml of bromine were then added dropwise at −70° C. over the course of 45 minutes. The reaction mixture was stirred for another 60 minutes and then warmed to room temperature. The solution was poured onto saturated sodium hydrogen-carbonate solution, the organic phase was separated and the aqueous phase was extracted with dichloromethane. The combined organic phases were dried and the solvent was removed in vacuo. Filtration through silica gel yielded a colourless oil.

Yield: 12 g (50% of theory).

EXAMPLE 6

30 g of the dithianylium trifluoromethanesulfonate obtained in Example 4 were intially charged in 250 ml of dichloromethane at −70° C. A solution of 14.8 ml of triethylamine and 11.6 g of 3,4-difluorophenol in 50 ml of dichloromethane was added dropwise at −70° C., which resulted in immediate precipitation of a colourless solid. The reaction mixture was stirred for another hour at −70° C. 57.2 ml of triethylamine tris-hydrofluoride were added dropwise and the mixture was stirred for another 5 minutes. 18.2 ml of bromine were then added dropwise over the course of 45 minutes. The reaction mixture was stirred for another 60 minutes at −70° C. and then warmed to room temperature. The solution was poured onto sodium hydrogencarbonate solution, the organic phase was separated and the aqueous phase was extracted with dichloromethane. The combined organic phases were dried and the solvent was removed. Filtration through silica gel yielded a colourless oil.

Yield: 8.1 g (34% of theory).

EXAMPLE 7

30 g of the dithianylium trifluoromethanesulfonate obtained in Example 4 were intially charged in 250 ml of dichloromethane at −70° C. A solution of 14.8 ml of triethylamine and 13.1 g of 3,4,5-trifluorophenol in 50 ml of dichloromethane was added dropwise which resulted in immediate precipitation of a colourless solid. The reaction mixture was stirred for another hour at −70° C. 57.2 ml of triethylamine tris-hydrofluoride were added dropwise and the mixture was stirred for another 5 minutes. 18.2 ml of bromine were then added dropwise over the course of 45 minutes. The reaction mixture was stirred for another 60 minutes and then warmed to room temperature. The mixture was poured onto sodium hydrogen-carbonate solution, the organic phase was separated and the aqueous phase was extracted with dichloromethane. The combined organic phases were dried and the solvent was removed in vacuo. Filtration through silica gel yielded a colourless oil.

Yield: 7.4 g (30% of theory).

EXAMPLE 8

10 g of 2,6-difluoro-4-(4-pentylcyclohexyl)benzoic acid, 3.5 ml of 1,3-propanedithiol and 8.5 ml of trifluoromethanesulfonic acid were mixed and stirred at room temperature for 15 minutes and at 110° C. for 20 min. The mixture was cooled to room temperature, 80 ml of diethyl ether were added, and the reaction mixture was stored at −20° C. overnight. The solid which had precipitated was filtered off with suction under nitrogen, washed with diethyl ether and dried in vacuo.

Yield: 10.3 g (60% of theory)

$^{13}$C NMR (CDCl$_3$, 303 K): $\delta_{carbenium}$=212 ppm.

EXAMPLE 9

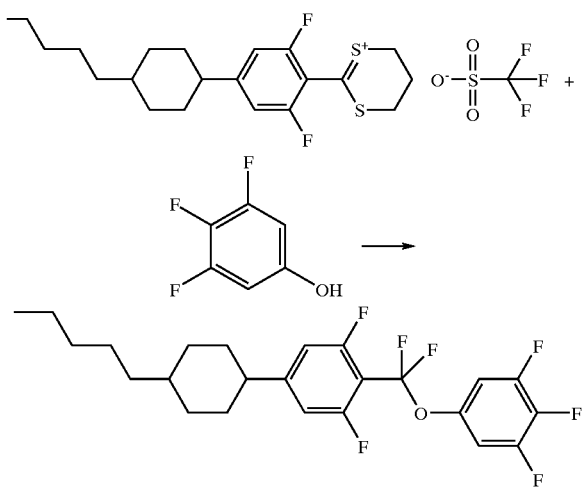

10 g of the solid obtained in Example 8 were dissolved in 100 ml of dichloromethane and admixed with a solution of 6.2 g of 3,4,5-trifluorophenol (90% in toluene) and 5.7 ml of triethylamine in 20 ml of dichloromethane at −75° C. The colourless clear solution was stirred for another 45 min and then 15.1 ml of triethylamine tris-hydrofluoride were added dropwise. 5 min later a suspension of 26.8 g of 1,3-dibromo-5,5-dimethylhydanthoin in 50 ml of dichloromethane was added in portions over the course of 45 min. The mixture was subsequently warmed to −20° C., and the orange solution was slowly added to an aqueous sodium hydrogensulfite/hydrogencarbonate solution. The organic phase was separated and the aqueous phase was extracted with dichloromethane. The combined organic phases were dried and the solvent was removed under reduced pressure.

Yield: 7.8 g of a slightly yellow solid (90% of theory)

EXAMPLE 10

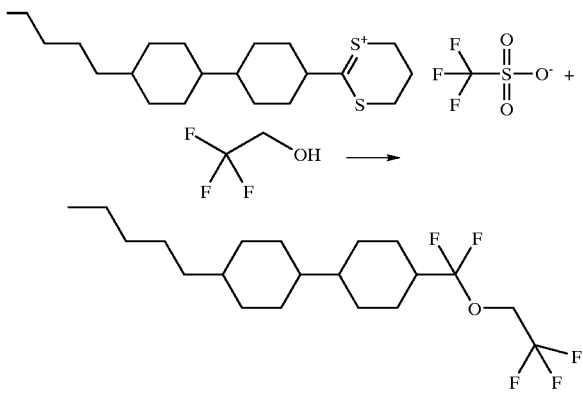

3.367 g of the dithianylium trifluoromethanesulfonate obtained in Example 2 were intially charged in 30 ml of dichloromethane at −70° C. and admixed with a mixture of 1.128 ml of triethylamine and 0.737 g of trifluoroethanol in 3 ml of dichloromethane, resulting in precipitation of a colourless solid. The reaction mixture was stirred for 1 h at −70° C., admixed with HF/pyridine (50%, equivalent to 66.97 mmol) and stirred for another 5 min. 1.715 ml of bromine in 15 ml of carbon tetrachloride were then added dropwise, a further 10 ml of dichloromethane were added and the mixture was stirred for another 60 minutes. The mixture was warmed to room temperature, and the yellow solution was carefully poured into 75 ml of saturated sodium hydrogencarbonate solution with stirring. After gas evolution had ceased, sodium hydrogencarbonate was added until weakly alkaline, the organic phase was separated and the aqueous phase was extracted three times with 30 ml of dichloromethane each time. The combined organic phases were washed with water and dried over sodium sulfate, and the solvent was removed in vacuo. The residue was filtered through silica gel using n-hexane. The raw product was recrystallized twice from pentane at −78° C. The product was stirred in pentane in the presence of basic alumina and copper powder overnight, filtered through silica gel using pentane and crystallized from pentane at −78° C.

Yield: 445.0 mg (crystallized product)

$^{19}$F NMR (235 MHz, CDCl$_3$) δ=−80.50 ppm (d, $^3$J=7.0 Hz, 2 F, CF$_2$O), −72.47 (m, 3F, CF$_3$)

| Melting point: | 19° C. |
|---|---|
| Clearing point: | 72° C. |

EXAMPLE 11

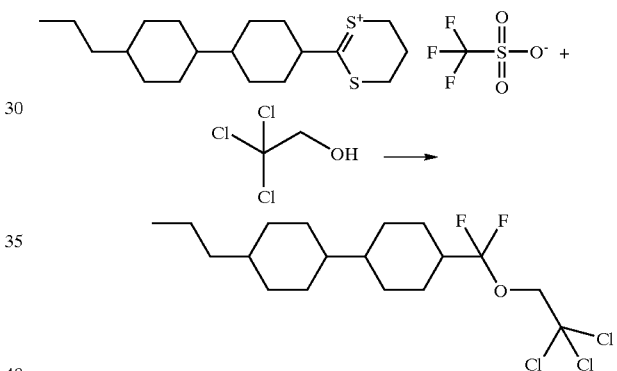

10.0 g of the dithianylium trifluoromethanesulfonate of the formula shown above which had been prepared similarly to the dithianylium triflate used in Example 2 were initially charged at −70° C. and 150 ml of dichloromethane were added. A mixture of 8.761 ml of triethylamine and 6.053 ml of trichloroethanol in 10 ml of dichloromethane was added dropwise, and the solution immediately turned yellow and a colourless solid precipitated. After addition was complete, the mixture was stirred for 1 h at −70° C. and then admixed with HF/pyridine (50%, equivalent to 210.670 mmol). After 5 min, 30.118 g of 1,3-dibromodimethylhydantoin, suspended in 50 ml of dichloromethane were added in portions over the course of about 20 min. The mixture was stirred for another 2 h and warmed to −30° C., and the orange suspension was poured into a stirred mixture consisting of 300 ml of saturated sodium hydrogencarbonate solution and 50 ml of sodium hydrogensulfite solution and being saturated with sodium hydrogen carbonate. The organic phase was separated and the aqueous phase was extracted twice with 100 ml of dichloromethane each time. The combined organic phases were washed with saturated sodium chloride solution and dried over sodium sulfate, and the solvent was removed in vacuo. The residue was filtered through silica gel using hexane. For further purification, the raw product was dissolved in ether, stirred in the presence of copper powder overnight, and again filtered through silica gel using hexane.

A slightly yellow oil was obtained which crystallized slowly. The raw product was crystallized twice from pentane at −20° C.

Yield: 2.498 g (29.2%)

$^{19}$F NMR (235 MHz, CDCl$_3$) δ=−81.18 ppm (d, $^3$J=8.2 Hz, 2 F, CF$_2$O) Melting point: 47° C.

EXAMPLE 12

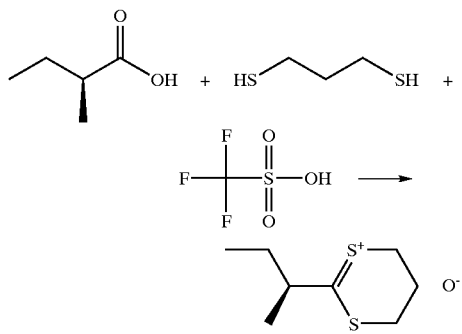

12.632 ml of trifluoromethanesulfonic acid were added dropwise to 5 g of (+)—S-2-methylbutyric acid and 5.352 ml of dimercaptopropane and the mixture was subsequently heated to 120° C. for 30 min. The mixture was cooled, admixed with 70 ml of ether and cooled to −78° C. with stirring. At the same temperature, the mother liquor was removed with suction using an immersion frit. The slightly yellow solid melted during warming to room temperature. The resulting yellow oil was admixed with 20 ml of ether, again frozen out with vigorous stirring and filtered off with suction. A slightly yellow solid was obtained which was stored on dry ice overnight and reacted without further purification.

EXAMPLE 13

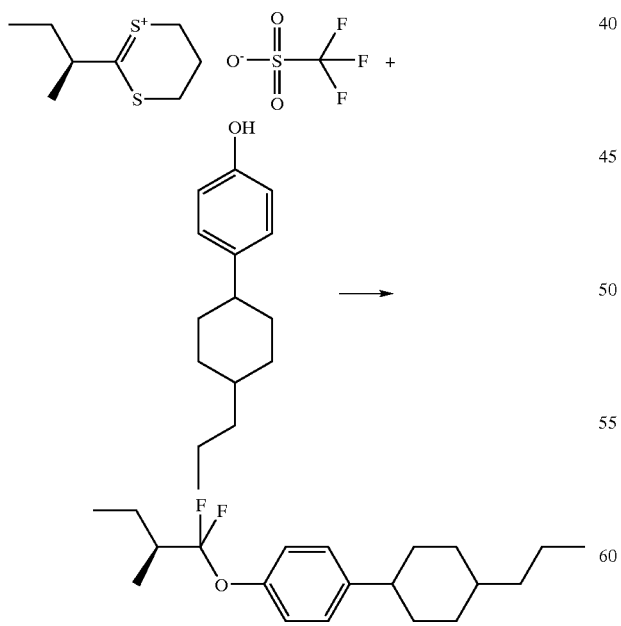

A solution of 10.48 g of the phenol and triethylamine (1.2 equivalents based on the phenol) in 75 ml of dichloromethane was slowly added dropwise to 7.78 g of the triflate prepared in Example 12 in 50 ml of dichloromethane at −70° C. The mixture was stirred for 1 h and admixed with 19.96 ml of triethylamine tris-hydrofluoride. Subsequently a solution of 6.147 ml of bromine in 30 ml of dichloromethane was added dropwise over the course of 1 h. The mixture was stirred for another 90 min, warmed to −20° C. and poured into 500 ml of ice-cold 1 M aqueous sodium hydroxide solution. The aqueous phase was separated and extracted three times with dichloromethane. The combined organic phases were vigorously stirred for 30 min in the presence of Celite, filtered, washed twice with water and dried over sodium sulfate. The solvent was removed in vacuo and the residue was filtered through silica gel using n-hexane. A colourless oil was obtained which was crystallized twice from n-pentane at −78° C.

Yield: 3.390 g (43.5%) of the twice-crystallized product $^{19}$F NMR (235 MHz, CDCl$_3$) δ=78.26 ppm (dd, $^3$J=9.1 Hz, $^3$J=11.5 Hz, 2 F, CF$_2$O) Melting point: 33° C.

What is claimed is:

1. Process for the preparation of compounds having at least one —CF$_2$O— bridge in the molecule, which comprises initially reacting a bis(alkylthio)carbenium salt with a compound containing at least one hydroxyl group in the presence of a base followed by oxidative fluorination, preferably in situ, with a fluorinating agent and an oxidizing agent to form the compound having at least one —CF$_2$O— bridge in the molecule.

2. Process according to claim 1, wherein the bis(alkylthio)carbenium salt has a structure of the formula (I)

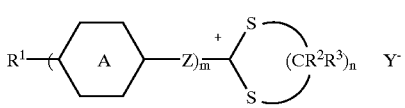

in which:

in each case independently of one another, is cis- or trans-1,4-cyclohexylene, 1,4-phenylene or 1,4-cyclohex-3-enylene, where these groups may also be monosubstituted or disubstituted by halogen, in particular fluorine, pseudohalogen, —OCF$_3$ or —OCHF$_2$, R$^1$ is a linear or branched alkyl or alkoxy radical having 1 to 12 carbon atoms which is unsubstituted, monosubstituted by —CN or —CF$_3$ or at least monosubstituted by halogen, a linear or branched oxyalkyl, alkenyl or alkenyloxy radical having 2 to 12 carbon atoms or a linear or branched oxalkenyl radical having 3 to 12 carbon atoms, where, in addition, one or more CH$_2$ groups in these radicals may, in each case independently of one another, be replaced by —O—, —S—, —CO—, —CO—O—, —O—CO— or —O—CO—O— in such a way that heteroatoms are not linked directly to one another, or halogen, Z is, in each case independently of one another, a single bond, a —CH$_2$—CH$_2$—, —CF$_2$—CF$_2$—, —CF$_2$—CH$_2$—, —CH$_2$—CF$_2$—, —CF=CF—, —CH=CH—, —C≡C—, —CO—O—, —O—CO—, —CF$_2$—O— or —O—CF$_2$— group, —S—(CR$^2$R$^3$)$_n$—S— is a bridge consisting of two sulfur atoms which are linked by a carbon chain having two or three carbon atoms, where the hydrocarbon bridge may also carry one or more substituents $R^2$ and $R^3$, in particular alkyl or alkylene groups, where, in addition, the radicals $R^2$ and $R^3$ may together form a cycloalkyl group or aryl group,

| | |
|---|---|
| m | is an integer from 0 to 6, |
| n | is 2 or 3, and |
| $Y^-$ | is any desired anion. |

3. Process according to claim 1, wherein the bis(alkylthio) carbenium salt contains a noncoordinating or weakly coordinating anion $Y^-$, in particular selected from the group consisting of tetrafluoroborate, hexafluorophosphate, perchlorate and perfluoroalkylsulfonate, in particular trifluoromethanesulfonate.

4. Process according to claim 1, wherein the compound containing at least one hydroxyl group is a phenol which may optionally be substituted, and in particular carries a polar group, preferably —F, —Cl, —CN, —NCS, —OCF$_3$ or —OCH$_2$F, or an alkyl, cycloalkyl or phenyl radical in 4-position which in turn may be substituted by alkyl, cycloalkyl or phenyl radicals, where, in addition, one to three hydrogen atoms of these groups may in each case also be replaced by fluorine or chlorine atoms and a —CH$_2$—CH$_2$—, —CF$_2$—CF$_2$—, —CF$_2$—CH$_2$—, —CH$_2$—CF$_2$—, —CF=CF—, —CH=CH—, —C≡C—, —C(O)O—, —O—CO—, —CF$_2$—O—, —O—CF$_2$—, —CH$_2$—O— or —O—CH$_2$— group may also be present between these radicals.

5. Process according to claim 1, wherein the oxidizing agent is a compound which releases halonium equivalents, and is in particular selected from the group consisting of dimethyldibromohydantoin, N-bromosuccinimide, N-iodosuccinimide, bromine, SOCl$_2$, SO$_2$ClF, nitrosonium and nitronium salts and Chloramin T.

6. Process according to claim 1, wherein the fluorinating agent is selected from the group consisting of aliphatic and aromatic amine/hydrogen fluoride complexes, and is in particular selected from the group consisting of pyridine/hydrogen fluoride complexes, NEt$_3$·3HF, melamine·HF and polyvinylpyridine·HF.

7. Bis(alkylthio)carbenium salt of the formula I

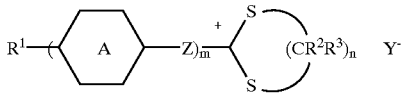
I in which $R^1$,

—S—(CR$^2$R$^3$)—S—, $Y^-$, m and n are as defined in claim 2.

8. Dithioorthoesters of the formula (II)

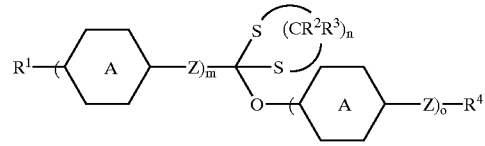
II in which $R^1$, $R^2$, $R^3$, Z,

m and n are as defined in claim 2, and $R^4$ is as defined for $R^1$ in claim 2, and, in addition, may be —H, —F, —Cl, —CN, —NCS, —OCF$_3$ or —OCHF$_2$, and o is an integer between 0 and 6.

9. Dithioorthoester according to claim 8, wherein a 1,4-phenylene group is present adjacent to the oxygen atom of the dithioorthoester functionality.

* * * * *

UNITED STATES PATENT AND TRADEMARK OFFICE
CERTIFICATE OF CORRECTION

PATENT NO. : 6,787,062 B2
DATED : September 7, 2004
INVENTOR(S) : Peer Kirsch et al.

It is certified that error appears in the above-identified patent and that said Letters Patent is hereby corrected as shown below:

Column 14,
Line 20, reads "Process for the preparation of compounds" should read -- A process for preparing a compound --.
Line 21, reads "which comprises initially" should read -- comprising --.
Line 24, reads "fluorination, preferably in situ," should read -- fluorination --.
Line 26, reads "to form the compound" should read -- to form a compound --.
Line 28, reads "Process" should read -- A process --.
Line 44, reads "in each case independently of one another, is cis- or trans" should read -- is, in each case independently of one another, a cis- or trans- --.
Line 46, reads "where these groups may also be" should read -- wherein each is optionally --.
Line 47, delete "in particular fluorine,".
Line 49, reads "is a linear" should read -- is halogen or a linear --.
Line 50, reads "is unsubstituted, mono-" should read -- unsubstituted, or mono- --.
Line 55, reads "where, in addition," should read -- wherein --.
Line 56, reads "in these radicals may," should read -- are optionally, --.
Line 57, reads "of one another, be replaced" should read -- of one another, replaced" --.
Line 60, reads "another, or halogen," should read -- another, --.
Lines 66 and 67 should be deleted.

Column 15,
Lines 1 to 5 should be deleted.
Line 6, insert -- $R^2$ and $R^3$ are, each independently, hydrogen, alkyl or alkylene, or two of $R^2$ and $R^3$ together form a cycloalkyl group or aryl group, --.
Line 10, reads "is any desired anion" should read -- is an anion --.
Lines 12 and 18, reads "Process" should read -- A process --.
Line 14, after "Y" delete ", in particular selected from the group consisting of tetrafluoroborate, hexafluorophosphate, perchlorate and perfluoroalkylsulfonate, in particular trifluoromethanesulfonate".
Line 20, reads "may optionally be substituted, and in particular carries a" should read -- is optionally substituted, with a --.
Line 21, delete "-F, -Cl, -CN, -NCS, -$OCF_3$ or -$OCH_2F$,".
Line 23, reads "in turn may be substituted by alkyl," should read -- is optionally substituted by an alkyl, --.
Line 24, reads "radicals, where in addition," should read -- radical, in which --.
Line 25, reads "of these groups may in each case also be" should read -- in each case independently and optionally are --.
Line 26, reads "chlorine atoms" should read -- chlorine atom --.
Line 31, reads "Process according to" should read -- A process according to --.
Line 33, delete "and is in particular selected from the group consisting of dimethyldibromohydanthoin, N-bromosuccinimide, N-iodosuccinimide, bromine, $SOCl_2$, $SO_2ClF$, nitrosonium and nitronium salts and Chloramin T".

Page 1 of 4

UNITED STATES PATENT AND TRADEMARK OFFICE
CERTIFICATE OF CORRECTION

PATENT NO. : 6,787,062 B2
DATED : September 7, 2004
INVENTOR(S) : Peer Kirsch et al.

It is certified that error appears in the above-identified patent and that said Letters Patent is hereby corrected as shown below:

Column 15 (cont'd),
Line 37, reads "Process according to" should read -- A process according to --.
Line 38, reads "agent is selected from the group consisting of aliphatic and" should read -- agent is an aliphatic and --.
Line 39, delete "complexes, and is in particular selected from the group consisting of pyridine/hydrogen fluoride complexes, NEt$_3$-3HF, melamine-HF and polyvinylpyridine-HF" and insert -- complex --.

Column 16,
Line 1, reads "Bis(alkylthio)carbenium salt of the formula I" should read -- A bis(alkylthio)carbenium salt of formula I --.
Line 9, delete "R$^1$,".

Line 10, delete "  , ".

Line 16, delete "-S-(CR$^2$R$^3$)-S-, Y, m and n are as defined in claim 2" and insert --  is, in each case independently of one another, a cis- or trans-1,4-cyclohexylene, 1,4-phenylene or 1,4-cyclohex-3-enylene, wherein each is optionally monosubstituted or disubstituted by halogen, pseudohalogen, -OCF$_3$ or -OCHF$_2$, R$^1$   is halogen or a linear or branched alkyl or alkoxy radical having 1 to 12 carbon atoms which is unsubstituted, or monosubstituted by -CN or -CF$_3$ or at least monosubstituted by halogen, a linear or branched oxyalkyl, alkenyl or alkenyloxy radical having 2 to 12 carbon atoms or a linear or branched oxalkenyl radical having 3 to 12 carbon atoms, wherein one or more CH$_2$ groups are optionally, in each case independently of one another, replaced by -O-, -S-, -CO-, -CO-O-, -O-CO- or -O-CO-O- in such a way that heteroatoms are not linked directly to one another, Z   is, in each case independently of one another, a single bond, a -CH$_2$-CH$_2$-, -CF$_2$-CF$_2$-, -CF$_2$-CH$_2$-, -CH$_2$-CF$_2$-, -CF=CF-, -CH=CH-, -C≡C-, -CO-O-, -O-CO-, -CF$_2$-O- or -O-CF$_2$- group, R$^2$ and R$^3$   are, each independently, hydrogen, alkyl or alkylene, or two of R$^2$ and R$^3$ together form a cycloalkyl group or aryl group, m   is an integer from 0 to 6, n   is 2 or 3, and Y   is an anion.

Line 17, reads "Dithioorthoesters of the formula (II)" should read -- A dithioorthoester of formula (II) --.
Line 27, delete "R$^1$, R$^2$, R$^3$, Z,".

Line 30, delete "  , ".

UNITED STATES PATENT AND TRADEMARK OFFICE
CERTIFICATE OF CORRECTION

PATENT NO. : 6,787,062 B2
DATED : September 7, 2004
INVENTOR(S) : Peer Kirsch et al.

It is certified that error appears in the above-identified patent and that said Letters Patent is hereby corrected as shown below:

Column 16 (cont'd),
Line 34, delete "m and n are as defined in Claim 2, and $R^4$ is as defined for $R^1$ in claim 2, and, in addition, may be -H, -F, -Cl, -CN, -NCS, -OCF$_3$ or -OCHF$_2$, and o is an integer between 0 and 6" and insert

   is, in each case independently of one another, a cis- or trans-1,4-cyclohexylene, 1,4-phenylene or 1,4-cyclohex-3-enylene, wherein each is optionally monosubstituted or disubstituted by halogen, pseudohalogen, -OCF$_3$ or -OCHF$_2$, $R^1$   is halogen or a linear or branched alkyl or alkoxy radical having 1 to 12 carbon atoms which is unsubstituted, or monosubstituted by -CN or -CF$_3$ or at least monosubstituted by halogen, a linear or branched oxyalkyl, alkenyl or alkenyloxy radical having 2 to 12 carbon atoms or a linear or branched oxalkenyl radical having 3 to 12 carbon atoms, wherein one or more CH$_2$ groups are optionally, in each case independently of one another, replaced by –O-, -S-, -CO-, -CO-O-, -O-CO- or –O-CO-O- in such a way that heteroatoms are not linked directly to one another, Z   is, in each case independently of one another, a single bond, a –CH$_2$-CH$_2$-, -CF$_2$-CF$_2$-, -CF$_2$-CH$_2$-, -CH$_2$-CF$_2$-, -CF=CF-, -CH=CH-, -C≡C-, -CO-O-, -O-CO-, -CF$_2$-O- or -O-CF$_2$- group, $R^2$ and $R^3$   are, each independently, hydrogen, alkyl or alkylene, or two of $R^2$ and $R^3$ together form a cycloalkyl group or aryl group, m   is an integer from 0 to 6, n   is 2 or 3, and Y   is an anion $R^4$   is -H, -CN, -NCS, -OCF$_3$, -OCHF$_2$, halogen or a linear or branched alkyl or alkoxy radical having 1 to 12 carbon atoms which is unsubstituted, or monosubstituted by -CN or -CF$_3$ or at least monosubstituted by halogen, a linear or branched oxyalkyl, alkenyl or alkenyloxy radical having 2 to 12 carbon atoms or a linear or branched oxalkenyl radical having 3 to 12 carbon atoms, wherein one or more CH$_2$ groups are optionally, in each case independently of one another, replaced by –O-, -S-, -CO-, -CO-O-, -O-CO- or –O-CO-O- in such a way that heteroatoms are not linked directly to one another, and o   is an integer between 0 and 6.

Line 38, reads "Dithioorthoester" should read -- A dithioorthoester --.
Line 42, add --

10.    (New) A process according to claim 1, wherein the oxidative fluorination is performed in situ.

11.    (New) A process according to claim 2, wherein

   is substituted with fluorine.

UNITED STATES PATENT AND TRADEMARK OFFICE
CERTIFICATE OF CORRECTION

PATENT NO. : 6,787,062 B2
DATED : September 7, 2004
INVENTOR(S) : Peer Kirsch et al.

It is certified that error appears in the above-identified patent and that said Letters Patent is hereby corrected as shown below:

Column 16 (cont'd), 12. (New) A process according to claim 1, wherein the bis(alkylthio)carbenium salt contains an anion Y⁻ which is tetrafluoroborate, hexafluorophosphate, perchlorate, perfluoroalkylsulfonate, or trifluoromethanesulfonate.

13. (New) A process according to claim 4, wherein the polar group is -F, -Cl, -CN, -NCS, $-OCF_3$ or $-OCH_2F$.

14. (New) A process according to claim 1, wherein the oxidizing agent is dimethyldibromohydanthoin, N-bromosuccinimide, N-iodosuccinimide, bromine, $SOCl_2$, $SO_2ClF$, nitrosonium a nitronium salt or Chloramin T.

15. (New) A process according to claim 6, wherein the complex is a pyridine/hydrogen fluoride complex, $NEt_3 \cdot 3HF$, melamine·HF or polyvinylpyridine·HF.

16. (New) A process according to claim 1, wherein the compound having at least one -$CF_2O$- bridge is a liquid crystal.

17. (New) A process according to Claim 1, wherein the bis(alkylthio)carbenium salt contains a noncoordinating anion Y⁻.

18. (New) A process according to claim 8, wherein $R^4$ is -F or -Cl.

19. (New) A process according to claim 2, wherein $R^1$ is F or Cl.

20. (New) A process according to claim 1, wherein the compound having at least one -$CF_2O$- bridge is a liquid crystal, an intermediate for a polymer, a pharmaceutically active compound or a crop protecting agent. --.

Signed and Sealed this

Twenty-seventh Day of December, 2005

JON W. DUDAS
*Director of the United States Patent and Trademark Office*